(12) United States Patent
Liu et al.

(10) Patent No.: US 9,066,960 B2
(45) Date of Patent: Jun. 30, 2015

(54) USE OF THE EFFECTIVE FRACTION OF ALKALOIDS FROM MULBERRY TWIG IN PREPARING HYPOGLYCEMIC AGENTS

(75) Inventors: Yuling Liu, Beijing (CN); Zhufang Shen, Beijing (CN); Zhen Chen, Beijing (CN); Renyun Wang, Beijing (CN); Xuejun Xia, Beijing (CN); Yueteng Chen, Beijing (CN); Quan Liu, Beijing (CN); Sujuan Sun, Beijing (CN); Mingzhi Xie, Beijing (CN)

(73) Assignee: INSTITUTE OF MATARIA MEDICA, CHINESE ACADEMY OF MEDICAL SCIENCES, Beijing (CN)

( * ) Notice: Subject to any disclaimer, the term of this patent is extended or adjusted under 35 U.S.C. 154(b) by 1224 days.

(21) Appl. No.: 12/674,532

(22) PCT Filed: Aug. 22, 2007

(86) PCT No.: PCT/CN2007/002540
§ 371 (c)(1),
(2), (4) Date: Feb. 22, 2010

(87) PCT Pub. No.: WO2008/025249
PCT Pub. Date: Mar. 6, 2008

(65) Prior Publication Data
US 2011/0130352 A1    Jun. 2, 2011

(30) Foreign Application Priority Data
Aug. 21, 2006   (CN) .......................... 2006 1 0111644

(51) Int. Cl.
*A61K 36/605* (2006.01)
(52) U.S. Cl.
CPC .................................. *A61K 36/605* (2013.01)

(58) Field of Classification Search
None
See application file for complete search history.

(56) References Cited

U.S. PATENT DOCUMENTS

| 4,994,572 A | * | 2/1991 | Fleet ............................ 546/220 |
| 2001/0018090 A1 | * | 8/2001 | Noda et al. .................... 426/597 |

FOREIGN PATENT DOCUMENTS

| CN | 1559539 A | 1/2005 |
| CN | 1742803 A | 3/2006 |

OTHER PUBLICATIONS

Asano (J. Agric. Food Chem. (2001), vol. 49, pp. 4208-4213).*
Asano (Carbohydrate Research (1994), vol. 259, pp. 243-255).*
CN 1742803—Mar. 2006 (English translation).*
International Search Report dated Nov. 15, 2007.

* cited by examiner

*Primary Examiner* — Susan Hoffman
(74) *Attorney, Agent, or Firm* — Scully, Scott, Murphy & Presser, P.C.

(57) ABSTRACT

The present invention relates to an effective fraction of alkaloids and the effective fraction is prepared from mulberry twig and its active ingredients are a composition of alkaloids. Determined by HPLC, the percentage of the total alkaloids are 50% or more by weight in the effective fraction and the percentage of the compound 1-deoxynojirimycin is 30% or more by weight in the total alkaloids. The effective fraction of the invention is prepared as the following steps: the mulberry twig is extracted by solvents, and the extract is precipitated by alcohol precipitation or flocculation to remove the impurities, and then concentrated, purified by resin chromatography. The present invention also relates to a pharmaceutical composition containing the said effective fraction of alkaloids and to the use of the effective fraction of alkaloids according to claim 1-4 in preparing hypoglycemic agents.

15 Claims, 1 Drawing Sheet

USE OF THE EFFECTIVE FRACTION OF ALKALOIDS FROM MULBERRY TWIG IN PREPARING HYPOGLYCEMIC AGENTS

FIELD OF THE INVENTION

The present invention relates to use of the effective fraction of alkaloids from mulberry twig for preparation of hypoglycemic agents.

DESCRIPTION OF RELATED ART

It is reported that the incidence of diabetes mellitus is up to 4% in the people over age of 40 and more than 11% in the people over age of 60 in China. According to the latest data from the WHO, the number of diabetic patients will quadruple in the next 15 years in China. Diabetes has become a serious disease that threatens human life and health. More than 90% of the patients with diabetes mellitus are suffered from type 2 diabetes and these patients have to take long-time oral hypoglycemic agents to control the hyperglycemia. At present, there are five classes of commercial oral hypoglycemic drugs including: (1) sulfonylureas, (2) biguanides, (3) α-glucosidase inhibitors, (4) insulin-sensitizing agent, (5) traditional Chinese medicine. In China, the annual sales of oral hypoglycemic drugs are more than 10 billion yuan.

In 1950s, oral hypoglycemic drugs such as sulfonylureas and biguanide came into the market, which enabled the patients with type 2 diabetes to control the blood glucose levels, prolong longevity and improve the quality of life. However, sulfonylurea oral agents tend to induce hypoglycemia and biguanides agents may cause serious side effects on gastrointestinal tract. After 40 years of effort, a new type of α-glucosidase inhibitor was found for the treatment of type 2 diabetes mellitus. The application of such agent has been recognized as a new way to control diabetes all over the world. The α-glucosidase inhibitor interacts with α-glucosidase located in the brush border of the small intestine. It can slow down the hydrolization of polysaccharides into monosaccharides, delay the absorption of glucose, postpone the postprandial blood sugar peaks, and reduce the range of "blood sugar fluctuations". Therefore, α-glucosidase inhibitor can reduce blood sugar, prevent and delay the development of certain chronic complications of diabetes. At the beginning of 1990s, the German Bayer Company introduced the new drug glucobay (Acarbose), which rapidly came into the markets of more than 50 countries and obtained a good therapeutic effect. In 1994, glucobay entered the Chinese market and after ten years of clinical practice, it has demonstrated to be effective and safe in the treatment of type 2 diabetes mellitus. Moreover, it has received a good social benefits and significant economic benefits.

There are abundant medicinal plants in China and there are numerous hypoglycemic crude preparations, while whose mechanisms of action are unknown and whose qualities are not controllable. Mulberry twig is the dry branch of *morus alba*, which contains hundreds of compounds, including polysaccharide, monosaccharide, vegetable protein, phenols, falconoid, saponin, organic acid, amino acid, polyhydroxy alkaloids, etc. In 1990s, Institute of Materia Medica, Chinese Academy of Medical Sciences discovered that the water and/or ethanol extract of mulberry twig had a strong α-glucosidase inhibitory activity and then applied for a Chinese patent "the application of ethanol and/or aqueous extract of Mulberry twig in preparation of hypoglycemic agent" (application NO. 97112359.4), which has been granted Apr. 10, 2002 by State Intellectual Property Office of PRC. As the dosage of crude preparation from ethanol and/or aqueous extract is too high and the quality is not controllable, Institute of Materia Medica, Chinese Academy of Medical Sciences carried out further studies on effective fraction of mulberry twig.

In addition to the aforementioned patent application 97112359.4, we retrieved another 3 pieces of patents related to mulberry extract with α-glucosidase inhibitor activity including:

A Chinese patent application 01113191.8, "Chinese medicinal extract with α-glucosidase inhibitor activity, and its preparation and application", disclosed a Chinese medicinal extract which is the total alkaloid from *Morus alba* L., mulberry leaves and mulberry fruit. It didn't refer to mulberry twig and had no description of the component of the alkaloid.

A Chinese patent application 02113004.3, "Extract of mulberry twig and its preparation and its novel use", referred to the total flavones but not to alkaloids. The extract was used to prevent hyperuricemia and gout but not diabetes.

A Chinese patent application 200410018677.4, "Medicinal composition possessing α-glucosidase inhibitor activity and its use", disclosed medicinal composition consisted of alkaloids and flavones. The alkaloids, whose weight ratio is 5-95%, are total alkaloids extracted from silkworm excrement, mulberry twig, *Morus alba* L. or mulberry leaves and the flavones extract, whose weight ratio is 10-95%, is at least one compound selected from the group consisting of catechin, quercetin and tea polyphenols. It didn't specifically disclose the content of total alkaloids in the alkaloid extract. In addition, the use of the combination of alkaloid extract and flavone extract in therapy only showed dose-additive effect, rather than have synergism under the experiment conditions.

Although *Morus alba* L. has highest content of alkaloids, but its plant resource is rare and the collection will bring damage to the plant. Mulberry leaf, which contains the lowest content of alkaloid, is hard to extract because it contains many impurities. There are abundant resources of Mulberry twig, which has moderate content of alkaloid between *Morus alba* L. and mulberry leaf, and it can be easily got by annually pruning. In addition, its price is inexpensive and its quality is controllable. Therefore, it has great practical significance to study the hypoglycemic effect of the effective fraction of alkaloids from mulberry twig.

DETAILED DESCRIPTION OF THE INVENTION

In view of the problems in crude preparation from ethanol and/or aqueous extract, the present invention takes a further research on the effective fraction of alkaloids from mulberry twig. Through the studies of α-glucosidase inhibitor activities of different extract fractions from mulberry twig, we discover that the water-soluble alkaloids show the strongest activity. In other words, the effective fraction with hypoglycemic activity exists in water-soluble alkaloids.

This invention is a further technical improvement based on CN97112359.4.

In order to achieve the purpose of the present invention, the invention uses the following technical solutions:

An effective fraction of alkaloids of the present invention is prepared from mulberry twig and the active ingredients are a composition of alkaloids; the content of the total alkaloids are 50% or more by weight in the effective fraction and the content of the compound 1-deoxynojirimycin is 30% or more by weight in the total alkaloids.

A preferred effective fraction of the invention includes at least one compound selected from the group consisting of N-methyl-1-deoxynojirimycin, fagomine, 3-epi-fagomine, 1,4-dideoxy-1,4-imino-D-arabinitol, 1,4-dideoxy-1,4- imino-D-ribitol, calysteginB$_2$, 2-O-(α-D-galactopyranosyl) -1-deoxynojirimycin, 6-O-(β-D-glucopyranosyl)-1-deoxynojirimycin and 1,4-dideoxy-1,4-imino -(2-O-β-D-glucopyranosyl)-D-arabinitol.

In a more preferred effective fraction of the invention, the percentage of the compound 1-deoxynojirimycin is 40% or more by weight in the total alkaloids.

In the most preferred effective fraction, the percentage of the compound 1-deoxynojirimycin is 50% or more by weight in the total alkaloids.

The present invention also discloses a method for preparing the effective fraction of alkaloids, that is: taking mulberry twigs as medicinal material, after smashing, extracting, separating, purifying and concentrating, the effective fraction, in which the content of the total alkaloids are 50% or more by weight, is prepared.

A method for preparing the effective fraction of alkaloids is described in detail as follows:

(a) the mulberry twig was extracted by solvents and the extract solution was concentrated, precipitated and removed impurities;

(b) the supernatant fluid was added into cation exchange resin and eluted with weak base eluent; and (c) the eluent was concentrated and added into anion exchange resin and the part not absorbed was collected, and dried to get the effective fraction powder.

Step (a) conducts as follows:

The said mulberry twig is preferably to be fresh one;

The preferred mulberry twig is dried and properly smashed in order to increase the contact areas with solvents and improve the efficiency.

The solvents are selected from the group consisting of water, alcohol, the mixture of water and alcohol, and acidic water; the preferred alcohols include methanol, ethanol, isopropanol, butanol, etc.; the most preferred solvent is water.

The amount of the solvent is 4-12 times of medicinal material and the extraction is repeated 1-3 times. The extraction can be carried out under static or dynamic conditions, preferably under dynamic conditions. In order to improve the efficiency of extraction, ultrasound can be used. The extraction is conducted at temperatures range from room temperature (eg 20° C.) to the solvent's reflux temperature, preferably at reflux temperature. The extraction process can be continuous or intermittent, wherein the intermittent process can be repeated 1-3 times. The extraction time ranges from 1 hour to 4 hours, preferably from 1.5 hours to 2.5 hours.

The precipitation prefers to be alcohol precipitation or flocculation, and 50-80% alcohol is used for flocculation.

Removal of impurities prefers by way of filtering or centrifugation.

Step (b) conducts as follows:

After adding the supernatant fluid into cation exchange resin, the resin is selectively washed with distilled water to remove the impurities not absorbed, before elunting with weak base water. This can improve the purity.

The preferred eluent is ammonia solution, whose concentration is preferably to be 0.2-1N.

Cation exchange resins are selected from sulfonic strong acid type and carboxylic week acid type; sulfonic strong acid type is preferred; the most preferred is 001×7(732#) cation resin.

The weight ratio of the crude drug and cation exchange resin is 1:0.1-0.5; more preferred to be 1:0.1-0.4; most preferred to be 1:0.2-0.3.

Step (c) conducts as follows:

After adding the concentrated eluent into anion exchange resin, the resin can be selectively washed by distilled water to collect all the compounds not absorbed and improve the final yield.

The drying methods include vacuum concentration, spray drying and freeze drying.

Anion exchange resins could be strong base type, such as quaternary amine (also known as quaternary amine) —NR$_3$OH(R is hydrocarbon group) or week base type, such as primary amine-NH$_2$, secondary amine-NHR, and tertiary amine —NR$_2$; preferably to be quaternary amine strong base type.

The most preferred resin is Dowex 1×2(OH$^-$) Anion exchange resin or 201×7(717, OH$^-$) Anion exchange resin.

The weight ratio of the crude drug and anion exchange resin is 1:0.2-0.8; preferred to be 1:0.3-0.7; most preferred to be 1:0.5-0.6.

Materials for ion exchange resin include styrene series, acrylic acid series, phenolic(FP) series, epoxy(EPA) series, vinyl pyridine(VP) series and urea-formaldehyde(UA) series; preferably to be styrene series.

The styrene resins mentioned here include gel type and macroporous type; the gel type is preferred.

The term "crude drug" mentioned in the present invention means the starting material mulberry twig.

A preferred preparation method is as follows:

(a) to every 350 kg of fresh mulberry twig, 2000 L of water is added and the mixture is refluxed for 2 hours, the extraction process was repeated 2 times, the extractions were combined and concentrated to a volume of 250 L. 250-270 L of ethanol is added to the concentrate. The mixture is precipitated for 24 hours and filtered;

(b) the supernatant fluid is added into 001×7(732#) cation exchange resin, whose dosage is crude drug: resin=1:0.2-0.3 by weight, washed with distilled water to neutral, then washed with 0.5N ammonia solution, and the eluent is collected;

(c) the eluent is added into Dowex 1×2(OH$^-$) Anion exchange resin or 201×7(717, OH$^-$) Anion exchange resin, whose dosage is crude drug: resin=1:0.5-0.6 by weight and the part not absorbed is collected and concentrated via vacuum concentration and dried to get a light brown powder.

Quantitative Determination of the Effective Fraction

As the alkaloids of the effective fraction are consisting of polyhydroxy alkaloids and their glycosides, which have no UV absorption, hence they have to be derived by derivatization reagents and then separated by HPLC. It is proved that this determination method have strong specificity, high sensitivity, and excellent repeatability.

It is found that in one class of alkaloids of the effective fraction, the content of 1-deoxynojirimycin is the highest and the activity is also the highest. So inventors prepared a refined 1-deoxynojirimycin which is used as a reference substance for determination. The refined 1-deoxynojirimycin is characterized by NMR, MS, IR, UV and the thermal analysis test and its structure is confirmed. The purity of refined 1-deoxynojirimycin is more than 98% and meets the quality requirement of reference substance.

Effective fractions of mulberry twig are prepared according to the above mentioned method. The said effective fraction is dissolved in water, and analyzed by pre-column derivatization HPLC using compound (1) as reference substance. Calculated by external standard method, the content of the total alkaloids is 50% or more in every effective fraction and the content of compound (1), 1-deoxynojirimycin, is 27% or more in the extract. In the effective fraction, the content of compound (1) is 27%÷50%=54% by weight.

Characterization of the Active Components in the Effective Fraction

The structures of the active components in the effective fraction are characterized by pre-column derivatization LC-MS/MS, and the results indicate that they are a class of polyhydroxy alkaloids, whose original structures are as follows:

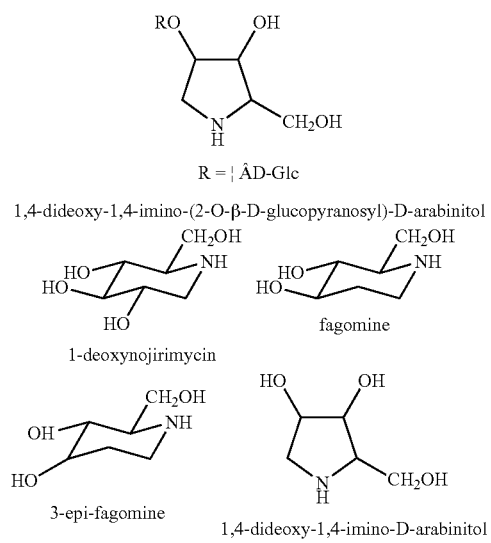

The Satability of the Effective Fraction

The effective fractions, obtained from pilot experiments, are stored sealed at room temperature, analyzed by HPLC at different time, and the results indicate that the quality is stable after 24 months. The results are listed in table 1.

TABLE 1

| | Content (%) | | | | |
|---|---|---|---|---|---|
| No | 0 months | 3 months | 6 months | 12 months | 24 months |
| 1 | 55.0% | 56.1% | 54.7% | 54.0% | 54.5% |
| 2 | 53.1% | 52.6% | 53.8% | 54.3% | 52.8% |
| 3 | 57.2% | 55.4% | 55.1% | 58.3% | 56.4% |

The effective fraction containing alkaloids can be mixed with pharmaceutically permitted excipients to form a variety of pharmaceutical compositions, mainly including oral dosage such as tablets, dispersible tablets, chewable tablets, capsules, granules, dripping pills or oral fluid. The content of the effective fraction of the alkaloids in the pharmaceutical composition is 12.5-300 mg per tablet, preferably 25-100 mg per tablet, even more preferably 50-100 mg per tablet, in terms of the total alkaloids.

In order to administer drugs and improve the therapeutic effect, the drug or the pharmaceutical composition can be administered by any known ways.

The dosage of the pharmaceutical composition can have a wide range of changes according to the nature and severity of the disease, the patient's individual circumstance, the administration route, the dosage form, etc. It can be administered in a dosage unit or divided into several dosage units, depending on the doctor's clinical experience, as well as the dosage regimen, including the use of other treatments.

The pharmaceutical composition can be taken alone or with other therapeutic drugs or symptomatic drugs. When there are synergies between the compound of the invention and other therapeutic drugs, its dosage should be adjusted to the actual situation.

In in vitro experiments, α-glucosidase inhibition percentages of the effective fraction of this invention were determined at different concentrations, using glucobay(Acarbose) as positive control, and the $IC_{50}$ values were computed. The results showed that in vitro the total alkaloids of mulberry twig had significant inhibitions of sucrase and maltase, and the inhibition of sucrase was stronger than glucobay, the inhibition of maltase was equal to glucobay, while the inhibition of amylase was significantly lower than glucobay, suggesting that the hypoglycemic activity of the effective fraction was equal to glucobay, but the side effects of gastrointestinal tract up gas might be less than glucobay.

Using glucobay as the control, the impacts of the effective fraction from mulberry twig on the curves of blood glucose of normal mice after loading sucrose and alloxan induced diabetic mice were studied. The results showed that at the dosage of 5-20 mg/kg in terms of the total alkaloids, the effective fraction from mulberry twig could significantly reduce elevated blood glucose of sucrose loaded mice, lower and postpone the peak of blood glucose, and blood glucose area under the curve was also significantly less than control group. This indicated that the alkaloids of the present invention could be used in preparing hypoglycemic drugs, which are used to control postprandial blood glucose of diabetic patients.

The advantages of the present invention are as follows:

The raw material is rich, inexpensive, and its quality is controllable.

The process is simple, and the cost is low.

The hypoglycemic activity of the effective fraction of the total alkaloids from mulberry twig was equal to glucobay, but the side effects of gastrointestinal tract up gas might be less than glucobay.

The α-glucosidase inhibitor activity $IC_{50}$ of the crude extracts from mulberry twig is about 60 μg/ml, while the $IC_{50}$ of the effective fraction of the total alkaloids from mulberry twig is less than 0.1 μg/ml, which is much better than the crude preparations from ethanol and/or aqueous extract of mulberry twig.

EXAMPLES

Figure 1:
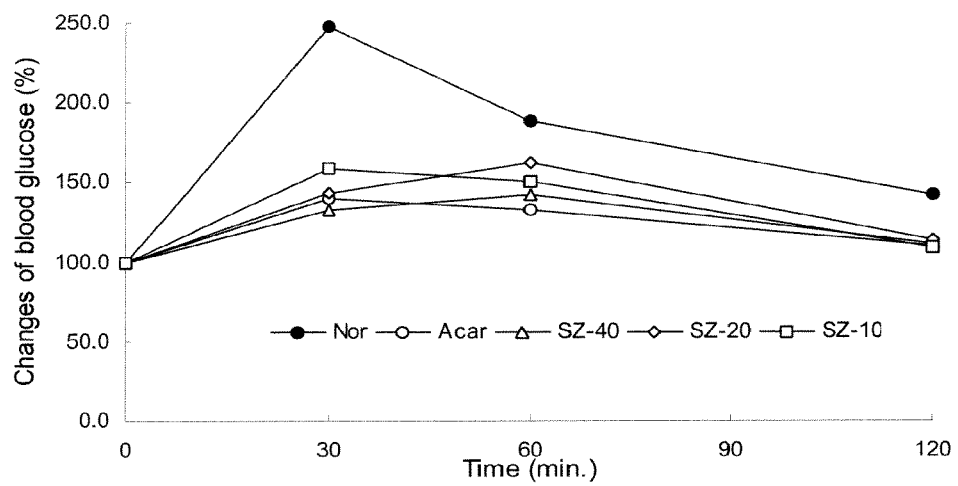
FIG. 1 is a graph showing that the impact of the effective fraction from mulberry twigs on the curves of blood glucose of normal mice after loading sucrose.

The invention disclosed herein is exemplified by the following examples of preparation, which should not be construed to limit the scope of the invention.

Preparations of the Effective Fraction of the Total Alkaloids

Example 1

The Preparation and Content Determination of the Effective Fraction of the Total Alkaloids Fresh mulberry twig was smashed and dried. To 350 kg of the dried mulberry twig, 2000 L of deionized water was added, and the mixture was refluxed for 2 hours. The extraction process was repeated 2 times, the extractions were combined and concentrated to 250 L, and then 700 L ethanol was added to the concentrate. The mixture was precipitated for 24 hours and filtered. The supernatant fluid was added into 001×7(732#) cation exchange resin, whose dosage is crude drug: resin=1:0.2 by weight, washed with distilled water to neutral, then washed with 0.5N ammonia solution, and the eluent was collected. The eluent was added into 201×7(717, OH⁻) Anion exchange resin, whose dosage is crude drug: resin=1:0.6 by weight and the part not absorbed was collected and concentrated via vacuum concentration and dried to get a light brown powder 530 g, yield 1.51‰.

Example 2

The Preparation and Content Determination of the Effective Fraction of the Total Alkaloids To another batch of dried fresh mulberry twig (350 kg), 2000 L of deionized water was added, and the mixture was refluxed for 2 hours. The extraction process was repeated 2 times, the extractions were combined and concentrated to 250 L, and then 700 L ethanol was added to the concentrate. The mixture was precipitated for 24 hours and filtered. The supernatant fluid was added into 001×7(732#) cation exchange resin, whose dosage is crude drug: resin=1:0.2 by weight, washed with distilled water to neutral, then washed with 0.5N ammonia solution, and the eluent was collected. The eluent was added into 201×7(717, OH⁻) Anion exchange resin, whose dosage is crude drug resin=1:0.6 by weight and the part not absorbed was collected and concentrated via vacuum concentration and dried to get a light brown powder 500 g.

Example 3

The Preparation and Content Determination of the Effective Fraction of the Total Alkaloids Fresh mulberry twig was smashed and dried. To 350 kg of the dried mulberry twig, 2000 L of deionized water was added, and the mixture was refluxed for 2 hours. The extraction process was repeated 2 times, the extractions were combined and concentrated to 250 L, and then 250 L ethanol was added to the concentrate. The mixture was precipitated for 24 hours and filtered. The supernatant fluid was added into 001×7(732#) cation exchange resin, whose dosage is crude drug: resin=1:0.2 by weight, washed with distilled water to neutral, then washed with 0.5N ammonia solution, and the eluent was collected. The eluent was added into 201×7(717, OH⁻) Anion exchange resin, whose dosage is crude drug: resin=1:0.5 by weight and the part not absorbed was collected and concentrated via vacuum concentration and dried to get a light brown porous powder 495 g.

Example 4

The Preparation and Content Determination of the Effective Fraction of the Total Alkaloids Fresh mulberry twig was smashed and dried. To 350 kg of the dried mulberry twig, 2000 L of deionized water was added, and the mixture was refluxed for 2 hours. The extraction process was repeated 2 times, the extractions were combined and concentrated to 250 L, and then 500 L ethanol was added to the concentrate. The mixture was precipitated for 24 hours and filtered. The supernatant fluid was added into 001×7(732#) cation exchange resin, whose dosage is crude drug: resin=1:0.3 by weight, washed with distilled water to neutral, then washed with 0.5N ammonia solution, and the eluent was collected. The eluent was added into Dowex 1×2(OH⁻) Anion exchange resin, whose dosage is crude drug: resin=1:0.5 by weight and the part not absorbed was collected and concentrated via vacuum concentration and dried to get a brown powder 520 g.

Preparation of Dosage Form

Example 1

Preparation of Tablets of Hypoglycemic Effective Fraction from Mulberry Twig 10 g of the effective fraction prepared in example 1, 5 g of calcium phosphate, 15 g of lactose, and 0.3 g of magnesium were respectively passed through 80 mesh sieves and mixed together. To the mixture, 70% ethanol was added to prepare damp mass, which was then granulated by passing through 20 mesh sieves, dried, then regulated by passing through 14 mesh sieves and pressed to tablets. Each tablet weighs about 300 mg and contains 100 mg of effective fraction extract, which is 50 mg of total alkaloids.

Example 2

Preparation of Capsules of Hypoglycemic Effective Fraction from Mulberry Twig 10 g of the effective fraction prepared in example 1, 5 g of calcium phosphate, 15 g of lactose, and 0.3 g of magnesium were respectively passed through 80 mesh sieves and mixed together. To the mixture, 70% ethanol was added to prepare damp mass, which was then granulated by passing through 20 mesh sieves, dried, regulated by passing through 40 mesh sieves and added into No. 2 hard capsules. The content of each capsule is about 100 mg and each capsule contains 100 mg of effective fraction extract, which is 50 mg of total alkaloids.

Example 3

Preparation of Oral Liquid of Hypoglycemic Effective Fraction from Mulberry Twig 10 g of the effective fraction prepared in example 1 was dissolved and diluted to 500 ml by distilled water, and then 0.05% of benzoic acid was added, flavoring agents could be selectively added, and the mixture was sub-packed in 5 ml or 10 ml of the vials and fitted with lids. Each bottle contains 100-200 mg of effective fraction extract, which is 50-100 mg of total alkaloids.

Example 4

Preparation of Dripping Pills of Hypoglycemic Effective Fraction from Mulberry Twig Taking 50 g of polyethylene glycol(PEG6000) and heated to melting (100° C.), and then 10 g of the effective fraction prepared in example 1 was added and stirred to get the molten liquid. The molten liquid was poured to the liquid storage tank of the pill machine, and then it was added dropwise to the liquid paraffin, cooling shaped and the paraffin was washed away, dried. Each dripping pill weighs about 30 mg and contains 5 mg of effective fraction extract, which is 2.5 mg of total alkaloids.

Example 5

Preparation Dispersible Tablets of Hypoglycemic Effective Fraction from Mulberry Twig 10 g of the effective fraction prepared in example 1, 20 g of calcium phosphate, 5 g of lactose, 15 g of mannitol, 10 g of cross-linked polyethylene pyrrolidone and 0.3 g of magnesium were respectively passed through 80 mesh sieves and mixed together. To the mixture, 70% ethanol was added to prepare damp mass, which was granulated by passing through 20 mesh sieves, dried, then regulated by passing through 14 mesh sieves and pressed to tablets. Each tablet weighs about 600 mg and contains 100 mg of effective fraction extract, which is 50 mg of total alkaloids.

Example 6

Preparation Chewable Tablets of Hypoglycemic Effective Fraction from Mulberry Twig 10 g of the effective fraction prepared in example 1, 5 g of calcium phosphate, 5 g of lactose, 15 g of mannitol and 0.3 g of magnesium were respectively passed through 80 mesh sieves and mixed together. To the mixture, 70% ethanol was added to prepare damp mass, which was granulated by passing through 20 mesh sieves, dried, then regulated by passing through 14 mesh sieves and pressed to tablets. Each tablet weighs about 300 mg and contains 100 mg of effective fraction extract, which is 50 mg of total alkaloids.

PARMALOGICAL EXPERIMENT

Example 1

In Vitro experiment

Using glucobay(Acarbose) as positive control, α-glucosidase inhibition percentages of the effective fraction in example 1 were determined at different concentrations, and the $IC_{50}$ values were computed. The results showed that, in vitro, the total alkaloids of mulberry twig had significant inhibitions of sucrase and maltase, and the inhibition of sucrase was stronger than glucobay, the inhibition of maltase was equal to glucobay, while the inhibition of amylase was significantly lower than glucobay, suggesting that the hypoglycemic activity of the effective fraction was equal to glucobay, but the side effects of gastrointestinal tract up gas might be less than glucobay. The results are listed in table 2.

TABLE 2

α-glucosidase inhibition activity of the effective fraction

| | $IC_{50}$ (ng/ml) | |
|---|---|---|
| | SZ-A | Arcarbose |
| sucrase | 21.9 | 87.1 |
| maltase | 40.4 | 39.3 |
| amylase | >10 mcg/ml | 2.4 mcg/ml |

Example 2

The Impact of the Effective Fraction on the Curves of Blood Glucose of Normal Mice After Loading Sucrose The test groups of the effective fraction set up three dosages, namely 10 mg/kg, 20 mg/kg, and 40 mg/kg (p.o.), as well as a negative control group (empty) and a positive control group (using glucobay as positive control drug, 10 mg/kg; p.o.). The results showed that the effective fraction of mulberry twig in the dosage of 10 mg/kg~40 mg/1 g can significantly reduce elevated blood glucose of sucrose loaded mice and the blood glucose area under the curve was also significantly less than control group. The results of test groups and positive control group have no significant differences (see FIG. 1).

Example 3

Figure 2:
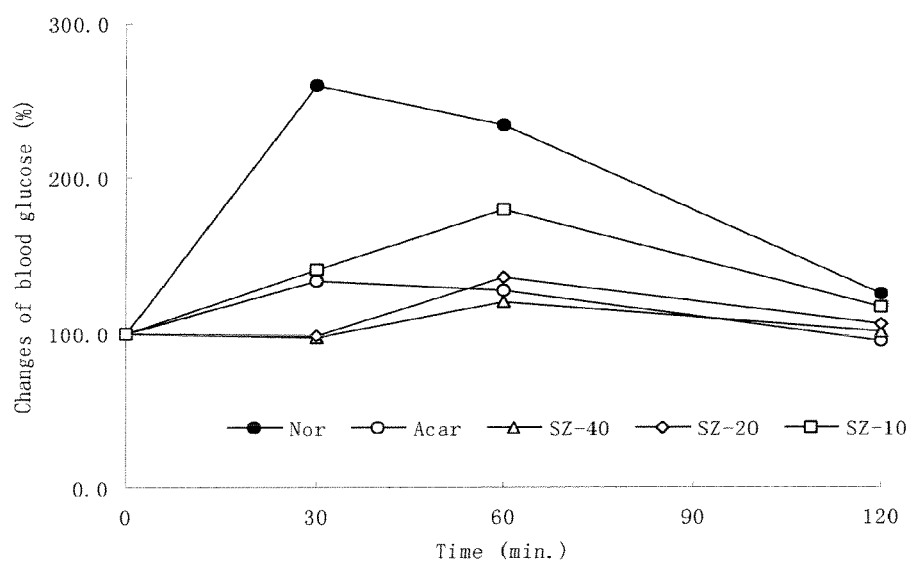
FIG. 2 is a graph showing that the impact of the effective fraction from mulberry twigs on the curves of blood glucose of alloxan induced diabetic mice after loading sucrose.

The Impact of the Effective Fraction on the Curves of Blood Glucose of Alloxan Induced Diabetic Mice after Loading Sucrose 5 groups of alloxan induced diabetic mice were divided to negative control group, positive control group using glucobay (10 mg/kg) and the varied dosage group (10 mg/kg, 20 mg/kg, 40 mg/kg). The results showed that the effective fraction of mulberry twig could lower and postpone the peak of blood glucose, and reduce the blood glucose area under the curve. The effects of 20 mg/kg and 40 mg/kg treatment groups were better than positive control group (see FIG. 2).

The invention claimed is:

1. A fraction of alkaloids having hypoglycemic activity, prepared by a process comprising:
   (a) extracting mulberry twig with solvents and precipitating the extract solution;
   (b) collecting the supernatant fluid, adding the collected supernatant fluid into cation exchange resin, and eluting the resin with a weak base eluent; and
   (c) collecting and concentrating the effluent, adding the concentrated effluent into anion exchange resin, collecting the part not absorbed to the anion exchange resin, and drying the collected part to obtain the fraction of alkaloids having hypoglycemic activity in powder,
   wherein the fraction of alkaloids having hypoglycemic activity comprises as the active ingredients a mixture of alkaloids, and wherein the percentage of the total alkaloids are 50% or more by weight in the fraction of alkaloids having hypoglycemic activity and the percentage of the compound 1-deoxynojirimycin is 30% or more by weight in the total alkaloids, and wherein hypoglycemic activity of the fraction as determined by the $IC_{50}$ of sucrase is 21.9 ng/ml.

2. The fraction of alkaloids according to claim 1, wherein said cation exchange resins are selected from sulfonic strong acid type or carboxylic weak acid type; and said anion exchange resins are selected from strong base type anion exchange resins or weak base type anion exchange resins.

3. The fraction of alkaloids according to claim 2, wherein said strong base type anion exchange resin is quaternary amine —$NR_3OH$ type, wherein R is hydrocarbon group; and said anion exchange resins are selected from the group consisting of primary amine—$NH_2$ type, secondary amine—NHR type, and tertiary amine —$NR_2$ type.

4. The fraction of alkaloids according to claim 2 or 3, wherein the materials for ion exchange resins are selected from the group consisting of styrene series, acrylic acid series, phenolic(FP) series, epoxy(EPA) series, vinyl pyridine (VP) series and urea-formaldehyde(UA) series.

5. The fraction of alkaloids according to claim 4, wherein said styrene series are selected from a gel type or a macroporous type.

6. The fraction of alkaloids according to claim 1, wherein said weak base eluent is 0.2-1N ammonia solution;
said cation exchange resin is 00 1×7(732#) cation resin; and
said anion exchange resin is Dowex 1×2(OH$^-$) Anion exchange resin or 201×7(717OH$^-$) Anion exchange resin.

7. The fraction of alkaloids according to claim 1, wherein:
in step (a), to every 350 kg of mulberry twigs, 2000 L of water is added and the mixture is refluxed for 2 hours, said extracting with solvents is repeated twice, the extractions are combined and concentrated to a volume of 250 L, 250-270 L of ethanol is added to the concentrate, and the mixture is precipitated for 24 hours and filtered;
in step (b), the supernatant fluid is added into 001×7(732#) cation exchange resin, with a ratio of supernatant fluid: resin=1:0.2-0.3 by weight, washed with distilled water to neutral, then washed with 0.5N ammonia solution, and the effluent is collected; and
in step (c), the effluent is added into Dowex 1×2(OH$^-$) Anion exchange resin or 201×7(717, OH$^-$) Anion exchange resin, with a ratio of effluent: resin=1:0.5-0.6 by weight, and the part not absorbed is collected and concentrated via vacuum concentration and dried to obtain a light brown powder.

8. The fraction of alkaloids according to claim 1, wherein the fraction also contains at least one compound selected from the group consisting of N-methyl-1-deoxynojirimycin, fagomine, 3-epi-fagomine, 1,4-dideoxy-1,4-imino-D-arabinitol, 1,4-dideoxy-1,4-imino-D-ribitol, calysteginB$_2$, 2-O-(α-D-galactopyranosyl)-1-deoxynojirimycin, 6-O-(β-D-glucopyranosyl)-1-deoxynojirimycin and 1,4-dideoxy-1,4-imino-(2-O-β-D-glucopyranosyl)-D-arabinitol.

9. The fraction of alkaloids according to claim 8, wherein the fraction also contains at least one compound selected from the group consisting of N-methyl-1-deoxynojirimycin, fagomine, 3-epi-fagomine, 1,4-dideoxy- 1,4-imino-D-arabinitol, 1,4-dideoxy-1,4-imino-D-ribitol, 6-O-(β-D-glucopyranosyl)-1-deoxynojirimycin, and 1,4-dideoxy-1,4-imino-(2-O-β-D-glucopyranosyl)-D-arabinitol.

10. The fraction of alkaloids according to claim 1, wherein the fraction further comprises the following compounds: fagomine, 3-epi-fagomine, 1,4-dideoxy-1,4-imino-D-arabinitol, and 1,4-dideoxy-1,4-imino-(2-O-β-D-glucopyranosyl)-D-arabinitol.

11. A pharmaceutical composition with hypoglycemic activity, comprising an effective dose of the fraction of alkaloids according to claim 1 and a pharmaceutically acceptable excipient.

12. The pharmaceutical composition according to claim 11, wherein said pharmaceutical composition is formulated as tablets, dispersible tablets, chewable tablets, capsules, granules, dripping pills or oral fluid.

13. The pharmaceutical composition according to claim 12, wherein the content of the fraction of alkaloids is 12.5-300 mg/tablet.

14. The pharmaceutical composition according to claim 12, wherein the content of the fraction of alkaloids is 25-100 mg/tablet.

15. The pharmaceutical composition according to claim 12, wherein the content of the fraction of alkaloids is 50-100 mg/tablet.

* * * * *